US011969073B2

(12) United States Patent
Chico

(10) Patent No.: US 11,969,073 B2
(45) Date of Patent: Apr. 30, 2024

(54) FALSE EYELASH CLEANSING DEVICE

(71) Applicant: Sarah Chico, Redondo Beach, CA (US)

(72) Inventor: Sarah Chico, Redondo Beach, CA (US)

(*) Notice: Subject to any disclaimer, the term of this patent is extended or adjusted under 35 U.S.C. 154(b) by 658 days.

(21) Appl. No.: 16/949,258

(22) Filed: Oct. 22, 2020

(65) Prior Publication Data
US 2021/0030140 A1 Feb. 4, 2021

(51) Int. Cl.
A45D 44/00 (2006.01)
A41G 5/02 (2006.01)
A45C 11/00 (2006.01)
A61L 2/10 (2006.01)
A61L 2/26 (2006.01)

(52) U.S. Cl.
CPC ............... A45D 44/00 (2013.01); A41G 5/02 (2013.01); A45C 11/008 (2013.01); A61L 2/10 (2013.01); A61L 2/26 (2013.01); A61L 2202/11 (2013.01); A61L 2202/17 (2013.01)

(58) Field of Classification Search
None
See application file for complete search history.

(56) References Cited

U.S. PATENT DOCUMENTS 1,060,810 A * 5/1913 Aylott ................ E04G 21/1808
33/404
11,484,077 B1 * 11/2022 Arsenault ................ A61L 2/24
2017/0119145 A1 * 5/2017 Munoz .................... F26B 25/22

* cited by examiner

Primary Examiner — Rita P Adhlakha
(74) Attorney, Agent, or Firm — CIONCA IP Law P.C.

(57) ABSTRACT

A false eyelash cleansing device having a compact, a false eyelash mold layer, and a false eyelash clamp layer is provided. The compact has a top and a tub, the top has an exterior surface and an interior surface and is adapted to cover the tub. The top is pivotally engaged to the tub. The false eyelash mold layer has an indentation to hold the false eyelashes and has a plurality of drainage holes adapted to let a solution drain. Furthermore, the false eyelash mold layer is adapted to be inserted into the tub. Additionally, the false eyelash clamp layer has a false eyelash clamp bar adapted to secure the false eyelash to the false eyelash mold layer. The false eyelash clamp layer is adapted to be inserted into the tub and cover the false eyelash mold layer.

17 Claims, 5 Drawing Sheets

FALSE EYELASH CLEANSING DEVICE

BACKGROUND OF INVENTION

1. Field of the Invention

The invention relates generally to false eyelashes and more specifically to cleaning and disinfecting false eyelashes.

2. Description of the Related Art

False eyelashes are known to be reusable, but usually cannot get the maximum amount of wears a company may claim they can due to makeup build-up, glue build-up, and losing their shape. Typically, users need to remove the false eyelashes and then carefully remove any debris that may have built-up while wearing them. This removal process can be tedious and can lead to many ruined false eyelashes because of how delicate the false eyelashes are. Some users may try to wash their false eyelashes but are not successful because of how fragile each false eyelash is under water. Additionally, false eyelashes are difficult to hold while washing because of their small size and there is no convenient spot to grip onto without ruining them.

Currently, false eyelashes can also be expensive for a single use item, which they become when user's do not know how to properly clean and care for them. Moreover, if users do manage to wash them, they usually lose their shape and are still unwearable. Washing false eyelashes is also a time-consuming process because of how delicate each false eyelash is and the time they take to dry.

Therefore, there is a need to solve the problems described above by proving a device and method for cleansing false eyelashes.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, an eyelash cleansing device having a compact, the compact having a top and a tub, the top having an exterior surface and an interior surface and being adapted to cover the tub, the top being pivotally engaged to the tub is provided. Thus, an advantage is a more efficient way to wash and rinse false eyelashes with a soap and water solution.

In another aspect, an eyelash cleansing device having a false eyelash mold layer having an indentation, the indentation being adapted to hold the false eyelashes and having a plurality of drainage holes adapted to let a solution drain, wherein the false eyelash mold layer being adapted to be inserted into the tub is provided. In another aspect, an eyelash cleansing device having a false eyelash clamp layer having a false eyelash clamp bar adapted to secure the false eyelash to the false eyelash mold layer, the false eyelash clamp layer being adapted to be inserted into the tub and cover the false eyelash mold layer is provided. Thus, an advantage is clean false eyelashes that are still in the proper shape to be functional for the user. The false eyelash clamp holds the lash in position while it dries. This allows the false eyelash to be the right shape for application.

In another aspect, an eyelash cleansing device having a UV light disposed on the interior surface of the top, the UV light being adapted to disinfect the false eyelash when the top covers the tub is provided. Thus, an advantage is sanitized false eyelashes. This may prevent bacteria build-up and lessen the chances of eye infections and diseases caused by bacteria from reusing makeup items.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1:
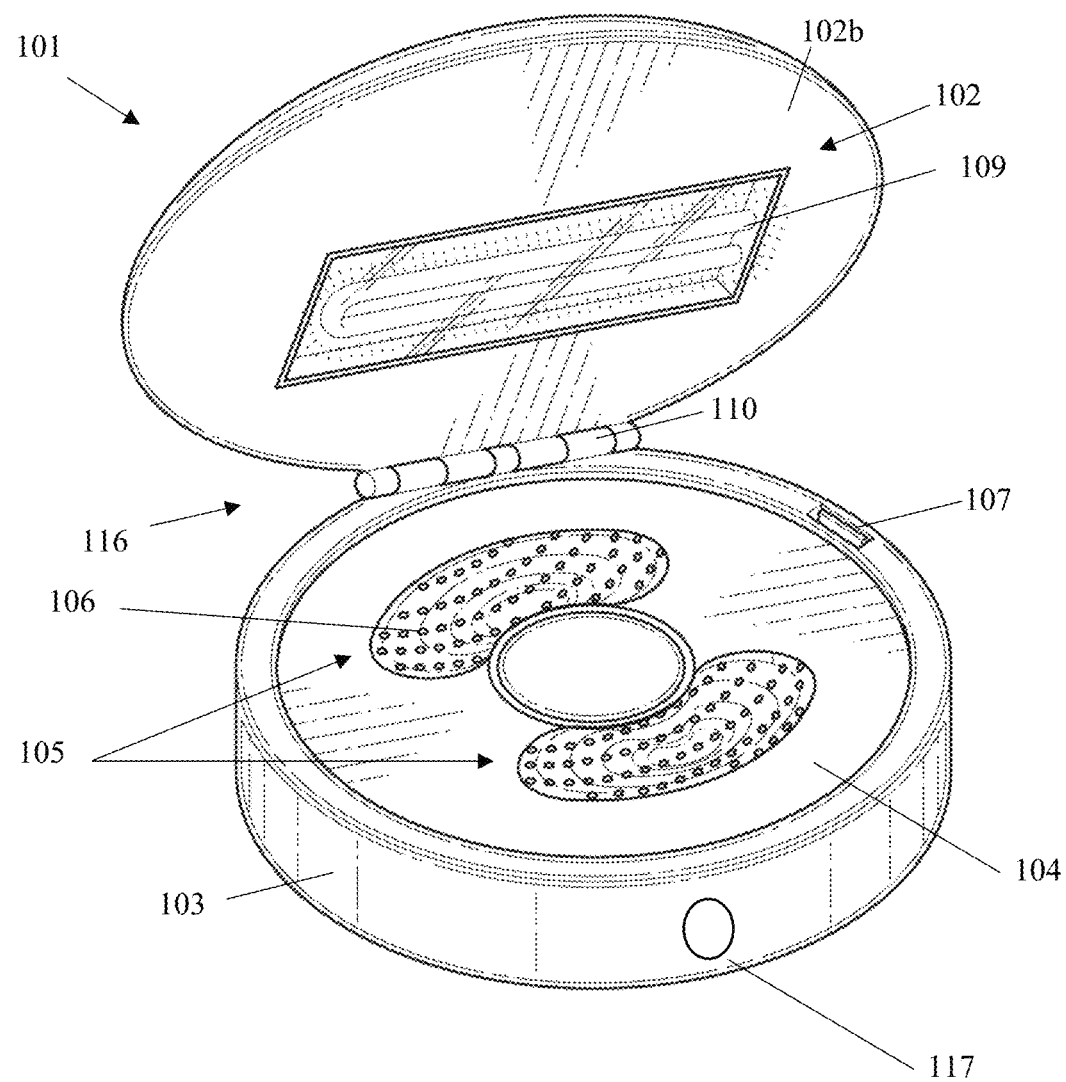
FIG. 1 illustrates the perspective view of a false eyelash cleansing device, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures (e.g., 105 and 205, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

FIG. 1 illustrates the perspective view of a false eyelash cleansing device 101, according to an aspect. The false eyelash cleansing device 101 being a compact 116 with a top 102 and a tub 103. As shown, the compact 116 may open and close with the top 102 being pivotally engaged with the tub 103. Additionally, the false eyelash cleansing device 101 having a false eyelash mold 105 with drainage holes 106 is provided. The false eyelash mold ("indentation," "false eyelash indentation") 105 being a portion of the false eyelash mold layer 104. As shown, the indentation 105 may be a portion of the false eyelash mold layer 104. In another example, the indentation 105 may be the entirety of the false eyelash mold layer 104. The false eyelash cleansing device 101 may also have a UV light 109, as shown. The UV light 109 may be used to further sanitize the false eyelashes during the cleansing process. The false eyelash cleansing device 101 may have a top 102 with the UV light 109.

In an example, the top 102 of the false eyelash cleansing device 101 may be attached to the tub 103 by a hinge 110. The pivotal engagement between the top 102 and the tub 103 allows the top 102 to close and seal onto the tub portion 103 of the false eyelash cleansing device 101. In an example, the mold layer 104 may be made of a silicone to hold its shape, prevent the false eyelashes from snagging, and would not be damaged from the constant use of water and the soap solution. In another example, the tub 103 may be a hard plastic or may also be made from silicone.

Cleaning false eyelashes is important because of the risk of bacteria entering the eye and being cost effective instead of using reusable false eyelashes only once. As described herein, false eyelashes are known to be reusable, but usually cannot get the maximum amount of wears a company may claim they can due to makeup build-up, glue build-up, and losing their shape. Typically, users need to remove the false eyelashes and then carefully remove any debris that may have built-up while wearing them. This removal process can be tedious and can lead to many ruined false eyelashes because of how delicate the false eyelashes are. Some users may try to wash their false eyelashes but are not successful because of how fragile each false eyelash is under water. Additionally, false eyelashes are difficult to hold while washing because of their small size and there is no convenient spot to grip onto without ruining them. Currently, false eyelashes can also be expensive for a single use item, which they become when user's do not know how to properly clean and care for them. Moreover, if users do manage to wash them, they usually lose their shape and are still unwearable. Washing false eyelashes is also time-consuming process because of how delicate each false eyelash is and the time they take to dry. Thus, properly cleaning and disinfecting false eyelashes is important.

The false eyelash cleansing device 101 having the UV light 109 may further sanitize the false eyelashes because of the UV light rays. The UV light 109 may be charged by a USB charger using the USB plug 107, as shown. A power source (not shown) may be used to power the UV light 109, which can be charged by the USB plug 107. In an example, when the top layer 102 closes the UV light 109 may turn on to initiate the disinfecting process. It should be understood the UV light 109 is configured to turn on when the compact is closed to prevent any harmful UV rays to be in contact with the user. In another example, the UV light 109 disposed on the interior surface 102b of the top 102 may turn on for approximately 30 seconds when the top 102 is closed to kill any germs and bacteria and will turn off automatically after the correct number of seconds are reached.

As shown, the false eyelash cleansing device 101 may be a cylindrical shape. In another example, the false eyelash cleansing device 101 may be a different shape (e.g., a square or rectangle). The cylindrical shape with a circular cross-section may be more compact because of how the circular shape mirrors the shape of the false eyelashes, which may decrease unusable space on the false eyelash cleansing device 101. For example, the various false eyelash cleansing device 101 shapes may also have a compartment 117 to contain additional spoolies or tweezers as described herein. The false eyelash cleansing device 101 may include the spoolies and tweezers to allow the users to have everything they need to clean and fluff their false eyelashes. Furthermore, a rectangularly shaped false eyelash cleansing device 101 may have all the components, such as a top 102 with the UV light 109, a tub 103, and a false eyelash clamp layer 213, as described herein.

Figure 2:
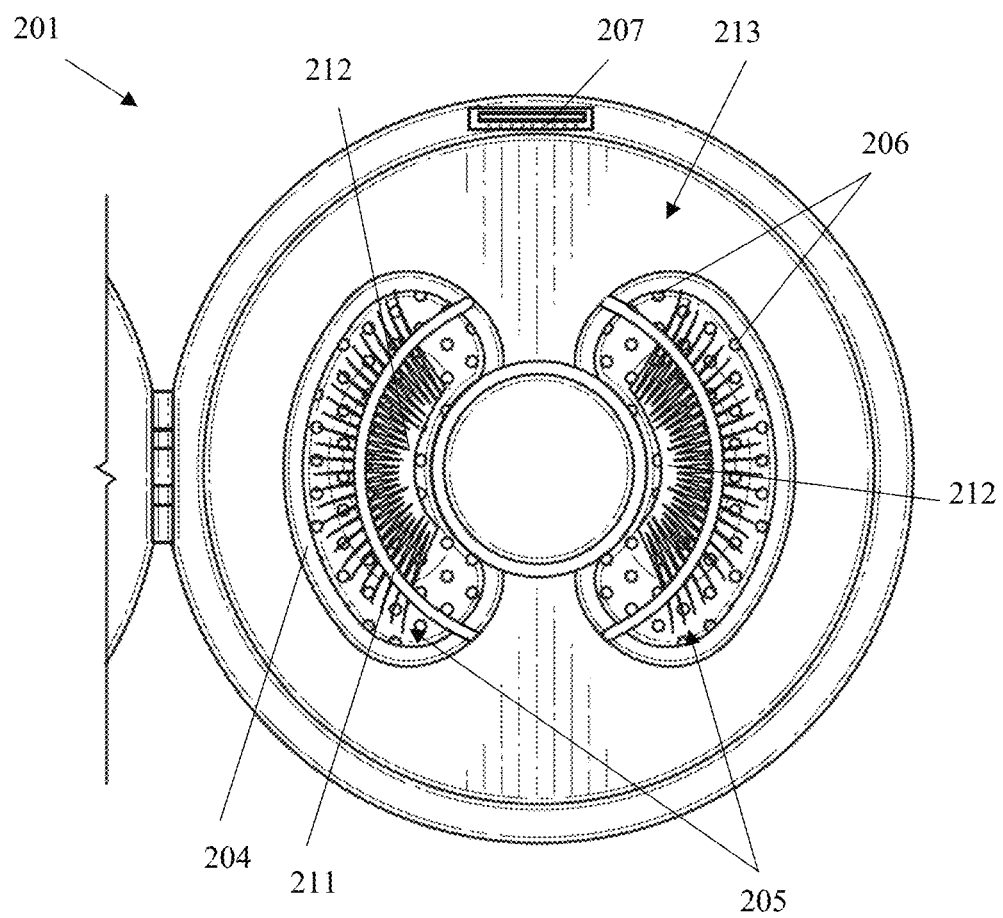
FIG. 2 illustrates the top view of a false eyelash cleansing device, according to an aspect.

FIG. 2 illustrates the top view of a false eyelash cleansing device 201, according to an aspect. The false eyelash cleansing device 201 having a false eyelash clamp layer 213 is provided. The false eyelash clamp layer 213 holds the false eyelashes in their curled form while they are drying. For example, the false eyelash clamp layer 213 may be coupled to the top 202 (e.g., attached), or in another example the false eyelash clamp layer 213 may be pivotally engaged with the top. As described herein, false eyelashes also commonly lose their shape after multiple wears and washes. The false eyelash clamp layer 213 allows the lashes to dry in their correct shape to further ensure the false eyelashes 212 maintain the correct form. The false eyelash clamp 211 may also secure the false eyelashes 212 in place during the washing process. The user would use the false eyelash cleansing device 201 to wash and sanitize the false eyelashes by filling the tub with a soap and water fluid mixture. For example, the user would then lower the lash mold layer 204 over the liquid filled tub, place the false eyelashes 212 in the indentation 205, and lower the false eyelash clamp layer 213 over the false eyelashes 212. The user may then close the top and, for example, shake the false eyelash cleansing device 201 to allow the soap and water fluid mixture to penetrate the drainage holes 206 to wash the false eyelashes 212. Also shown is the USB plug 207 for powering the UV light, which as described herein would disinfect and sanitize the false eyelashes.

Moreover, the false eyelash clamp 211 holds the false eyelashes in place within the false eyelash cleansing device 201, allowing the user to also store their false eyelashes within the false eyelash cleansing device 201. The plurality of drainage holes 206 also allows the false eyelashes to dry evenly because of the water draining and airflow around each false eyelash. The indentation may be a standard size to hold typical false eyelash 212 shapes and sizes. In another example, the indentation 205 and the false eyelash clamp 211 may be different corresponding shapes and sizes to fit a variety of different types of false eyelashes. The indentation 205, for example, may be different depths to account for different lengths in false eyelashes 212. For example, the indentation 205 may be large enough to hold false eyelashes 212 with a length up to 15 mm. In another example, the indentation 205 may be large enough to hold false eyelashes 212 with a length up to 25 mm.

The user may also use the false eyelash indentation 205 on the false eyelash mold layer 204 with the false eyelash clamp layer 213 to reshape false eyelashes 212. For example, the user may sleep with their false eyelashes 212 on and may get a kink from laying and pressing against the pillow for too long. The user would then place their false eyelashes 212 into the false eyelash indentation 205 with the false eyelash clamp layer 213 and allow them to curl properly. The user may also use a spoolie to further fluff their false eyelashes while they are reshaping. Additionally, the false eyelash cleansing device 201 may be used to rejuvenate the false eyelashes 212 without performing the cleansing process. For example, if the user wanted to rejuvenate a pair of clean false eyelashes 212, they may place their false eyelashes 212 into the false eyelash indentation 205 with the false eyelash clamp layer 213 to reshape and fluff the false eyelashes 212, thus, rejuvenating the false eyelashes 212 for future uses.

For example, the false eyelash mold layer 204 may snap into place within the compact. In another example, the false eyelash clamp layer 213 may snap into place within the compact.

Figure 3:
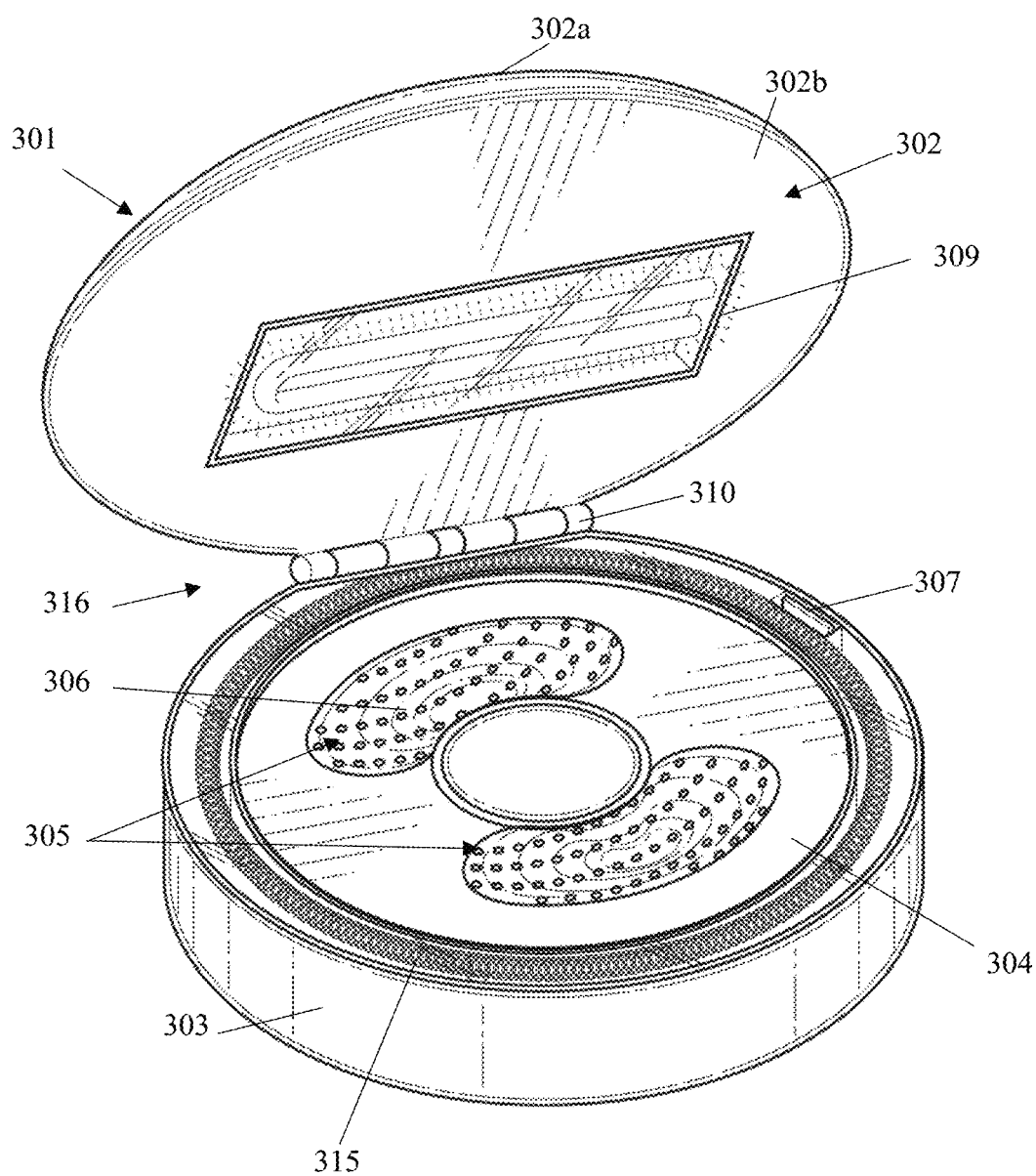
FIG. 3 illustrates the perspective view of a false eyelash cleansing device, according to an aspect.

FIG. 3 illustrates the perspective view of a false eyelash cleansing device 301, according to an aspect. The false eyelash cleansing device 301 may have a heat source to help the false eyelashes dry. Furthermore, the false eyelash cleansing device 301 may also have a UV coil 315 as shown. For example, the UV coil 315 may also be a small portion within the false eyelash cleansing device 301. The UV coil 315 would help the false eyelashes to dry faster by heating up within the false eyelash cleansing device 301. In another example, false eyelash cleansing device 301 may have an infrared light to allow the false eyelashes to dry. The UV coil 315 may also be charged by a USB charger using the USB plug 307, as shown. Additionally, the UV coil 315 may be powered by a power source (not shown). For example, the UV coil 315 may have an on and off switch (not shown) to allow the user to initiate the additional drying when needed.

As described herein, the false eyelash cleansing device 301 having a compact 316 having a top 302 and a tub 303, the top having an exterior surface 302a and an interior surface 302b and being adapted to cover the tub 303 is provided. The top 302 is pivotally engaged with the tub 303, as shown by the hinge 310. The false eyelash mold layer 304 has an indentation 305, the indentation 305 is adapted to hold the false eyelashes and has a plurality of drainage holes 306 adapted to let a solution drain, wherein the false eyelash mold layer 304 is adapted to be inserted into the tub 303. The false eyelash clamp layer has a false eyelash clamp bar (shown in FIG. 2) adapted to secure the false eyelash to the false eyelash mold layer 304, the false eyelash clamp layer being adapted to be inserted into the tub 303 and cover the false eyelash mold layer 304. The false eyelash cleansing device 301 may have a UV light 309, which may be disposed on the interior surface 302b of the top 302. The UV light 309 may be adapted to disinfect the false eyelash when the top covers the tub. The false eyelash cleansing device 301 may have also a UV coil 315, which may be disposed on the inside the tub 303. The UV coil 315 may be adapted to dry the false eyelash when the top 302 covers the tub 303. Moreover, the UV light 309 and UV coil 315 would in contact with a power source (not shown) to dry and disinfect the false eyelashes.

Figure 4:
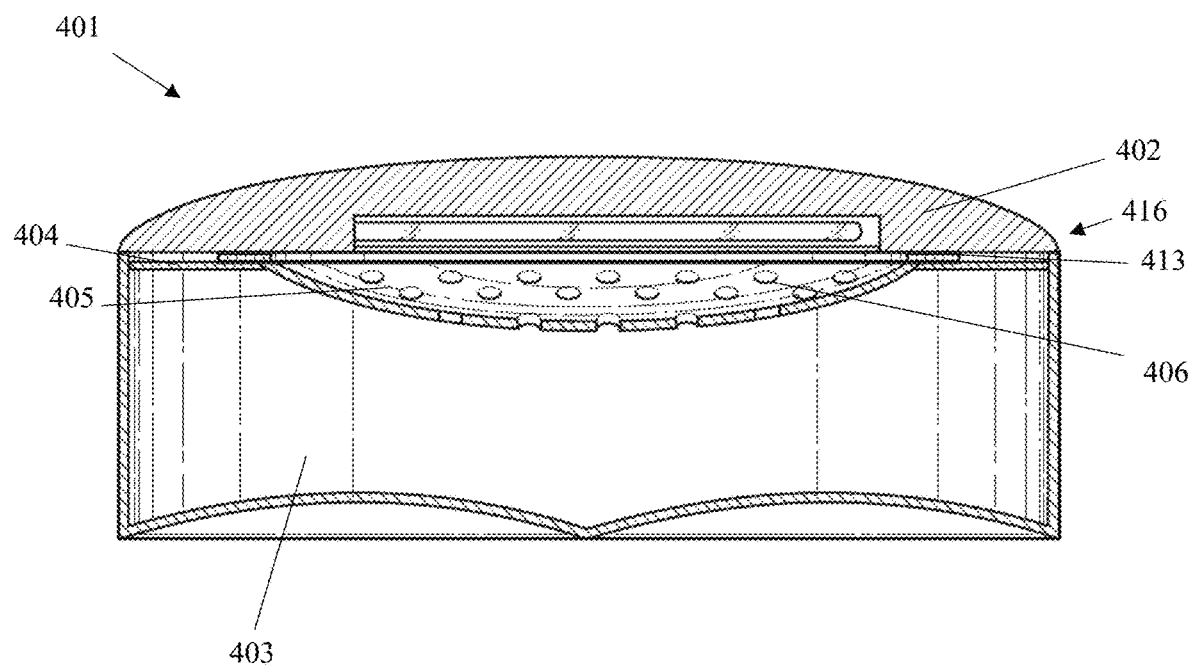
FIG. 4 illustrates the cross-sectional view of a false eyelash cleansing device, according to an aspect.

FIG. 4 illustrates the cross-sectional view of a false eyelash cleansing device 401, according to an aspect. The layers of the false eyelash cleansing device 401 are shown in FIG. 4. In an example, the false eyelash mold layer 404 and the false eyelash clamp layer may also be pivotally engaged within the compact 416, which would allow the layers to be within the compact 416 at all times.

For example, the tub layer ("tub layer" or "bathing bin") 403 may be filed with a cleaning solution (i.e., water and soap) by the user. The user would fill the tub layer 403 with solution but leave enough room for the false eyelash mold 405 to not be submerged in the liquid. Once the user fills the tub layer 403 to the desired fullness the user would lower the false eyelash mold layer 404 into the device 401. After the false eyelash mold layer 404 is placed inside the tub 403 the user would insert their false eyelashes that need to be cleaned and/or sanitized. The user would then insert the lash clamp layer 413 to hold the false eyelashes in place and in their curled form. The user would then close the top cover 402 to begin the cleansing process.

In an example, when the top layer 402 closes the UV light 409 may turn on to initiate the disinfecting process. In another example, the false eyelash cleansing device 401 may have a on and off switch to initiate the disinfecting process utilizing the UV light. Furthermore, as an example, the false eyelash cleansing device 401 may have compartments for the false eyelash tools, such as the tweezers, spoolies, and glue. The compartments may be underneath the tub 402 or, for example, may be within the tub 402 but separated from the solution by a divider. In another example, the compartments for the false eyelash tools, such as the tweezers, spoolies, and glue may be in the top layer 402.

The user may then shake, swirl, or rotate the false eyelash cleansing device 401 to thoroughly wash and sanitize the false eyelashes depending on how delicate the false eyelash is. After the user has thoroughly rinsed the false eyelashes with the solution, the user would remove the false eyelash mold layer 404 and dump the dirty water solution. The user then would insert the false eyelash mold layer 404 back into the compact and then may brush the false eyelashes to remove the glue, makeup, and debris. The user may use a spoolie, tweezers or another method to help remove the debris particles from the false eyelashes. The solution loosens the glue, makeup, and debris to make cleaning easier and less time consuming. The user may also user tweezers to further remove any of the debris that is stuck to the false eyelashes. When the false eyelashes are completely dry, the user would use a clean spoolie to fluff and fix the false eyelashes before applying. For example, the user may let the false eyelashes dry over night to ensure they are completely dry before reapplication. The user may then flip the compact 416 over to further help the false eyelashes dry in their desired curled form.

In another example, the user may soak their false eyelashes within the tub 403. Once the false eyelashes have soaked in the solution within the tub 403 the user may clean the lashes with the spoolie and tweezers. The spoolie may be used to brush and remove any particles that may be on the false eyelash. The user may also use tweezers to remove any glue or debris on the false eyelashes. After the user uses the tub 403 to soak and clean the false eyelashes, the user may empty the dirty solution from the tub 403 and dry the tub 403. The user then may insert the false eyelash mold layer 404 into the tub portion 403 of the false eyelash cleansing device 401. Once the false eyelash mold layer 404 has been inserted the user may place the clean false eyelashes into the false eyelash indentation 405. For example, the false eyelash mold layer 404 may be made of silicone, or other similar materials, in order to hold different lash sizes and dimensions. Additionally, the false eyelash indentation 405 may vary in size and shape to fit a variety of different types of false eyelashes. The user may then apply the false eyelash clamp layer 413 to secure the false eyelash in place. For example, the false eyelash clamp layer 413 may also be pivotally attached to the tub 403 and the top 402. In another example, the false eyelash clamp layer 413 may be removably attached to the tub 403. Furthermore, the user may apply external heat from a dryer to further speed up the drying process of the false eyelashes. As described herein, the false eyelash clamp layer 413 may press down on the false eyelashes, which may give them the desired curl.

Moreover, prior to letting the false eyelashes dry overnight, the user would insert the false eyelash clamp layer 413 on top of the wet false eyelash. The user would then spread the false eyelashes evenly and fully with a spoolie to ensure they dry in the appropriate shape.

Figure 5:
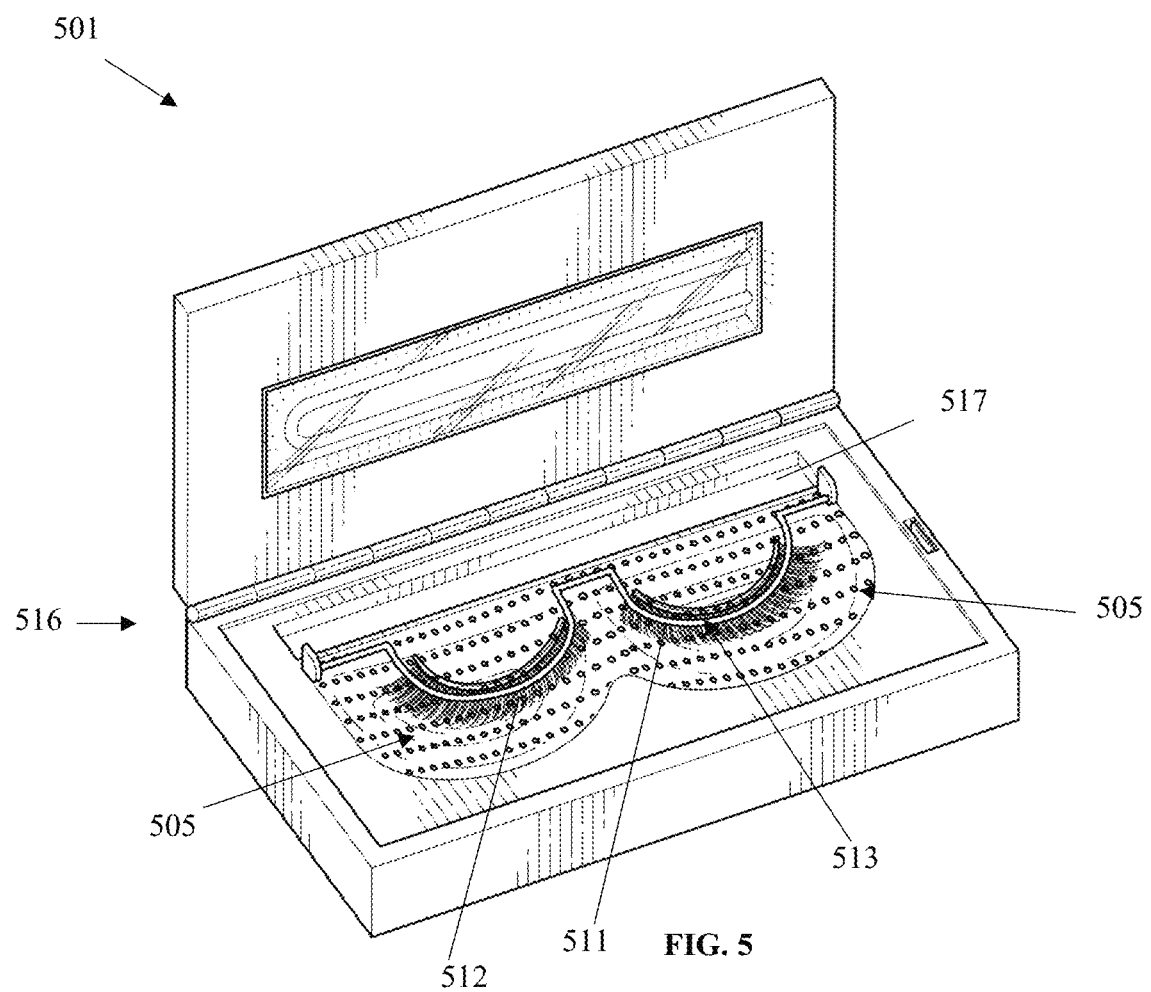
FIG. 5 illustrates the perspective view of a false eyelash cleansing device, according to an aspect.

FIG. 5 illustrates the perspective view of a false eyelash cleansing device 501, according to an aspect. As described herein, the false eyelash cleansing device 501 may be rectangular as shown. For example, in the rectangle embodiment, there may be a compartment 517 for tweezers or spoolies. Additionally, the lash clamp 511 may be pivotally attached to the compact 516. In another example, the false eyelash clamp layer 513 of the false eyelash cleansing device 501 may be the false eyelash clamp 511 on a hinge. Also, as an example, the indentation 505 for each of the false eyelashes 512 may be connected, as shown. The rectangular false eyelash cleansing device 501 may allow the user to cleanse the false eyelash 512 by the methods described in reference to FIG. 4.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A false eyelash cleansing device comprising:
   a compact having a top and a tub, the top having an exterior surface and an interior surface and being adapted to cover the tub, the top being pivotally engaged to the tub;
   a false eyelash mold layer having an indentation, the indentation being adapted to hold the false eyelashes and having a plurality of drainage holes adapted to let a solution drain, wherein the false eyelash mold layer being adapted to be inserted into the tub;
   a false eyelash clamp layer having a false eyelash clamp bar adapted to secure the false eyelash to the false eyelash mold layer, the false eyelash clamp layer being adapted to be inserted into the tub and cover the false eyelash mold layer;
   a UV light disposed on the interior surface of the top, the UV light being adapted to disinfect the false eyelash when the top covers the tub, and
   a UV coil adapted to dry the false eyelashes.

2. The false eyelash cleansing device of claim 1, wherein the false eyelash cleansing device is a cylindrical shape.

3. The false eyelash cleansing device of claim 1, wherein the false eyelash cleansing device has a spoolie compartment.

4. The false eyelash cleansing device of claim 1, wherein the false eyelash mold layer and the compact are pivotally engaged.

5. The false eyelash cleansing device of claim 1, wherein the false eyelash clamp layer and the compact are pivotally engaged.

6. The false eyelash cleansing device of claim 1, wherein the false eyelash clamp layer is coupled to the top.

7. A false eyelash cleansing device comprising:
- a compact having a top and a tub, the top having an exterior surface and an interior surface and being adapted to cover the tub, the top being pivotally engaged to the tub;
- a false eyelash mold layer having an indentation, the indentation being adapted to hold the false eyelashes and having a plurality of drainage holes adapted to let a solution drain, wherein the false eyelash mold layer being adapted to be inserted into the tub;
- a false eyelash clamp layer having a false eyelash clamp bar adapted to secure the false eyelash to the false eyelash mold layer, the false eyelash clamp layer being adapted to be inserted into the tub and cover the false eyelash mold layer;
- a UV coil disposed on the inside the tub, the UV coil being adapted to dry the false eyelash when the top covers the tub.

8. The false eyelash cleansing device of claim 7, further comprising a UV light adapted to disinfect the false eyelashes in the compact.

9. The false eyelash cleansing device of claim 7, wherein the UV coil is lining the entire interior of the compact.

10. The false eyelash cleansing device of claim 7, wherein false eyelash mold layer has two indentations.

11. The false eyelash cleansing device of claim 7, wherein the false eyelash mold layer snaps into the compact.

12. The false eyelash cleansing device of claim 7, wherein the false eyelash cleansing device is a rectangular shape.

13. The false eyelash cleansing device of claim 7, wherein the false eyelash cleansing has a tweezer compartment.

14. The false eyelash cleansing device of claim 7, wherein the false eyelash mold layer is silicone.

15. A false eyelash cleansing device comprising:
- a compact having a top and a tub, the top having an exterior surface and an interior surface and being adapted to cover the tub, the top being pivotally engaged to the tub;
- a false eyelash mold layer having an indentation, the indentation being adapted to hold the false eyelashes and having a plurality of drainage holes adapted to let a solution drain, wherein the false eyelash mold layer being adapted to be inserted into the tub;
- a false eyelash clamp layer having a false eyelash clamp bar adapted to secure the false eyelash to the false eyelash mold layer, the false eyelash clamp layer being adapted to be inserted into the tub and cover the false eyelash mold layer, and
- a UV coil, wherein the UV coil is adapted to line the entire interior of the compact.

16. The false eyelash cleansing device of claim 15, further comprising a UV light.

17. The false eyelash cleansing device of claim 15, wherein the compact is plastic.

\* \* \* \* \*